(12) United States Patent
Carrel-Billiard et al.

(10) Patent No.: US 12,329,865 B2
(45) Date of Patent: Jun. 17, 2025

(54) SELF-SANITIZING SYSTEM FOR VEHICLE CABINS

(71) Applicant: Accenture Global Solutions Limited, Dublin (IE)

(72) Inventors: Marc Carrel-Billiard, Vence (FR); Mary Elizabeth Hamilton, San Mateo, CA (US); Edy S. Liongosari, San Jose, CA (US)

(73) Assignee: Accenture Global Solutions Limited, Dublin (IE)

(*) Notice: Subject to any disclaimer, the term of this patent is extended or adjusted under 35 U.S.C. 154(b) by 841 days.

(21) Appl. No.: 17/565,540

(22) Filed: Dec. 30, 2021

(65) Prior Publication Data

US 2022/0202973 A1 Jun. 30, 2022

Related U.S. Application Data

(60) Provisional application No. 63/132,432, filed on Dec. 30, 2020.

(51) Int. Cl.
*A61L 2/10* (2006.01)
*A61L 2/24* (2006.01)

(52) U.S. Cl.
CPC ...... *A61L 2/10* (2013.01); *A61L 2/24* (2013.01); *A61L 2202/11* (2013.01); *A61L 2202/14* (2013.01); *A61L 2202/25* (2013.01)

(58) Field of Classification Search
CPC ..... A61L 2/10; A61L 2/24; A61L 9/20; A61L 2202/11; A61L 2202/14; A61L 2202/25; A61L 2209/111; B60H 1/00371; B60H 1/00742; B60H 3/0078
See application file for complete search history.

(56) References Cited

U.S. PATENT DOCUMENTS

| | | | |
|---|---|---|---|
| 7,175,807 B1* | 2/2007 | Jones | A61L 2/10 250/493.1 |
| 9,676,250 B2 | 6/2017 | Weast et al. | |
| 11,524,783 B2* | 12/2022 | Hack | B60Q 3/41 |

(Continued)

FOREIGN PATENT DOCUMENTS

| CN | 108839596 A | * 11/2018 | ............ A61L 2/10 |
|---|---|---|---|
| KR | 20150137293 | 12/2015 | |

OTHER PUBLICATIONS

AutoFutures.tv [online], "Combating Coronavirus and Other Bugs—Keeping Your Car Clean, Odourless & Disinfected," Feb. 24, 2020, retrieved on Aug. 11, 2020, retrieved from URL <https://www.autofutures.tv/2020/02/24/how-to-keep-your-car-virus-free/>, 5 pages.

(Continued)

*Primary Examiner* — Jennifer Wecker
*Assistant Examiner* — Brady C Pilsbury
(74) *Attorney, Agent, or Firm* — Polsinelli PC

(57) ABSTRACT

This document describes self-sanitizing systems that sanitize the cabins of vehicles. In one aspect, a method includes initiating a sanitizing cycle for sanitizing one or more surfaces of one or more components of a vehicle cabin. During the sanitizing cycle, one or more UV light sources are activated, and at least one of a shape, a position, or orientation of the surface is adjusted with respect to the one or more UV light sources. The sanitizing cycle is terminated.

18 Claims, 9 Drawing Sheets

(56) References Cited

U.S. PATENT DOCUMENTS

| | | | |
|---|---|---|---|
| 2015/0343102 A1* | 12/2015 | Romo | A61L 2/10 |
| | | | 436/1 |
| 2016/0220716 A1* | 8/2016 | Childress | B64D 11/02 |
| 2016/0280160 A1 | 9/2016 | MacNeille et al. | |
| 2019/0091738 A1 | 3/2019 | Chen | |
| 2020/0061223 A1* | 2/2020 | Hallack | A61L 2/24 |
| 2020/0307472 A1* | 10/2020 | Line | B60R 15/00 |
| 2021/0290809 A1* | 9/2021 | Salter | B60S 1/64 |
| 2021/0350689 A1* | 11/2021 | Kelly | G08B 21/245 |
| 2022/0008575 A1* | 1/2022 | Sood | H04R 1/028 |
| 2022/0031876 A1* | 2/2022 | Ubale | A61L 2/24 |

OTHER PUBLICATIONS

CNet.com [online], "Uber and Lyft vehicles are often germy, but this device wants to keep them clean," Sep. 20, 2019, retrieved on Aug. 11, 2020, retrieved from URL<https://www.cnet.com/roadshow/news/rideshare-vehicles-uber-lyft-germs-wellness-pod/>, 3 pages.
GHSP.com [online], "GHSP Announces Debut of UV-C Technology Brand grenlite™ at CES," Jan. 6, 2020, retrieved on Aug. 11, 2020, retrieved from URL<https://www.ghsp.com/news/ghsp-announces-debut-of-uv-c-technology-brand-greenlite-at-ces>, 3 pages.
ThePointsGuy.com [online], "JetBlue to trial 'GermFalcon' UV light machine on its planes," Jul. 29, 2020, retrieved on Aug. 11, 2020, retrieved from URL <https://thepointsguy.com/news/jetblue-germfalcon-honeywell-uv-cabin-system/>, 5 pages.

* cited by examiner

SELF-SANITIZING SYSTEM FOR VEHICLE CABINS

CROSS-REFERENCE TO RELATED APPLICATIONS

This application claims the benefit of U.S. Patent Application No. 63/132,432, filed Dec. 30, 2020, which is incorporated herein by reference.

FIELD

This specification generally relates to self-sanitizing systems for vehicle cabins.

BACKGROUND

The cabin of some vehicles are contacted by multiple people on a routine basis. For example, rideshare vehicles, taxis, buses, trains, and airplanes can routinely carry multiple people in each seat of the vehicle each day. The cabins can be cleaned manually, but such cleaning is often insufficient in killing viruses, germs, bacteria, and other pathogens between passenger occupancies. Further, manual cleaning may take more time and the quality of the results may vary significantly.

SUMMARY

This specification generally describes self-sanitizing systems that sanitize the cabins of vehicles. During each sanitizing cycle, the system can activate a light source, such as an ultraviolet (UV) light or far-UVC light. Such light sources have been shown to kill pathogens, such as viruses, germs, bacteria, and other microorganisms. The light source can be arranged within the cabin to illuminate the surface of the seats and/or other appropriate surfaces, e.g., of hand rests, door handles, etc. The light sources can be located in or on the dash of vehicles, seatbacks for second or higher seat rows, doors, the ceiling, or other appropriate locations.

According to some implementations, a self-sanitizing method includes initiating a sanitizing cycle for sanitizing one or more surfaces of one or more components of a vehicle cabin. During the sanitizing cycle, one or more UV light sources are activated, and at least one of a shape, a position, or orientation of the surface is adjusted with respect to the one or more UV light sources. The sanitizing cycle is terminated.

Implementations may include one or more of the following features. In some implementations, the one or more UV light sources include one or more far-UVC light sources.

Adjusting a shape of the surface can include activating one or more actuation zones of at least one surface, wherein each actuation zone comprises a plurality of cells that adjust a shape of the surface multiple times during the sanitizing cycle.

Initiating the sanitizing cycle can include detecting a change of state event indicating (i) that an occupant of the vehicle cabin has departed the vehicle cabin and (ii) a change of state from a clean vehicle cabin to a dirty vehicle interior, and initiating the sanitizing cycle in response to detecting the change of state event. Detecting the change of state event can include detecting that a color of thermochromic material of at least one surface is within a specified color range.

In some implementations, initiating the sanitizing cycle can include detecting that a sanitizing zone that comprises the one or more surfaces is unoccupied. Optionally, the sanitizing zone can be monitored during the sanitizing cycle to ensure that the sanitizing zone remains unoccupied.

In some implementations, terminating the sanitizing cycle includes detecting that a color of photochromic material of at least one surface is within a specified color range, and terminating the sanitizing cycle in response to detecting that the color of the photochromic material of the at least one surface is within a specified color range.

In some implementations, adjusting at least one of a shape, position, or orientation of the surface with respect to the one or more UV light sources includes determining that an area of the surface of the component has not been sufficiently sanitized and adjusting the orientation or position of the component such that the area is illuminated by the one or more light sources.

Some implementations can include detecting a contaminant on at least one surface and generating a notification that indicates that the vehicle cabin is in an unclean state. The notification can indicate one or more recommended manual interventions to clean the vehicle cabin.

The methods in accordance with the present disclosure can include any combination of the aspects and features described herein. That is, methods in accordance with the present disclosure are not limited to the combinations of aspects and features specifically described herein, but also may include any combination of the aspects and features provided.

The subject matter described in this specification can be implemented in particular embodiments so as to realize one or more of the following advantages.

The systems can initiate a sanitizing cycle in response to detecting a change of state event. The change of state event can be a change in temperature of a surface within the cabin, e.g., a change in temperature of a surface of a seat or a temperature within a particular temperature range, or a surface temperature within a particular temperature range. The change in temperature or temperature range can be indicative that a person was occupying the cabin or particular seat in the cabin, but has left the cabin or seat. Thus, the state of change event can indicate that a change from occupancy to non-occupancy of a cabin or seat. In this way, the system can target the sanitizing cycle to regions of the vehicle cabin that are likely to have been exposed to viruses, germs, bacteria, and other pathogens carried by passengers. At the same time, the overall duration of the sanitizing cycle may be kept relatively short, e.g., relative to sanitizing an entire cabin when only a small area of the cabin was occupied.

As the shape and configuration of these surfaces are not uniform, flat surfaces that can be easily illuminated, the system can change the shape, orientation, and/or position of the surfaces within the cabin during sanitizing cycles to ensure that all or appropriate areas of the surfaces are sanitized. For example, the system can activate an actuator to lift, fold, or unfold a seat so that a light source on a dash or seatback can sanitize the front portion of the seat or the underside of the seat. This provides clear access for sanitizing areas in front of and/or below the lower portion of the seat.

The system can use various signals to trigger sanitizing cycles, determine the duration of the sanitizing cycle, to change the shape, orientation, and/or position of the surfaces. For example, the system can include cameras for detecting changes in color of thermochromic threads in fabric of the surfaces. The thermochromic fabrics change color with exposure to heat. The system can use the detected colors to detect when a person has departed a cabin or seat. The cameras can also be used to detect the color of photochromic pigment in the fabric or panels of seats or other components to determine when a surface has been properly sanitized. The color of a photochromic pigment changes with exposure to UV light. When the system detects a particular color or color range, the system can terminate the sanitizing cycle. If there are areas of a surface that did not change to the particular color or color range, the system can adjust the shape, orientation, and/or position of the surface so that the area is properly sanitized and changes to the particular color or color range. This ensures that all surfaces that were or may have been contacted are sufficiently sanitized.

The seats and other components of the cabin can include actuation zones embedded therein. The system can activate these actuation zones to change the shape of the surfaces. The actuation zones can include cells that change the shape of the surface. By changing the shape of the surface, the light source can illuminate portions of the surface that would otherwise not be properly illuminated for sanitization.

Using cameras to initiate, control, and terminate sanitizing cycles, can provide a low power solution that can be implemented in vehicles where power is limited, such as automobiles and especially electric-powered automobiles to conserve power for other processes, such as powering an automobile.

In some implementations, the sanitizing controller can initiate a cleaning cycle for only particular surfaces, control the sanitizing cycle to focus on or better sanitize particular surfaces, or to ensure that all surfaces are sufficiently sanitized, and/or determine when the terminate a sanitizing cycle, e.g., when all surfaces are sufficiently sanitized.

The details of one or more implementations of the present disclosure are set forth in the accompanying drawings and the description below. Other features and advantages of the present disclosure will be apparent from the description and drawings, and from the claims.

BRIEF DESCRIPTION OF THE DRAWINGS

Like reference numbers and designations in the various drawings indicate like elements.

DETAILED DESCRIPTION

Figure 1A:
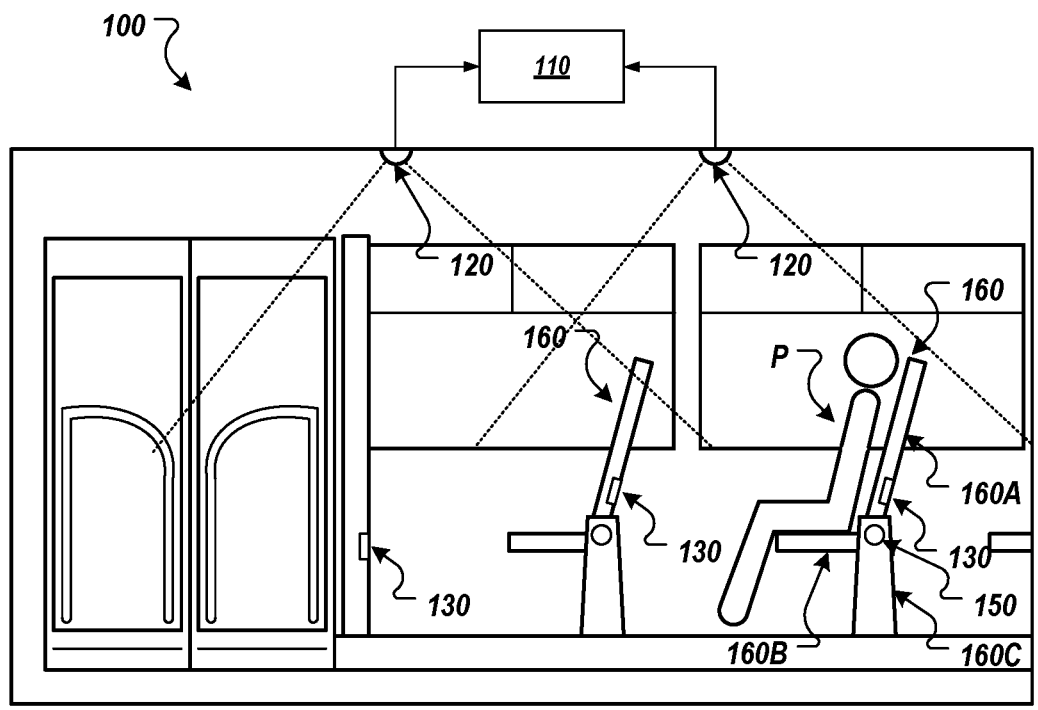
FIGS. 1A to 1E depict an example self-sanitizing system.

This specification generally describes self-sanitizing systems that sanitize the cabins of vehicles. For example, the systems can be implemented in an automobile (e.g., gas-powered or electric-powered cars, trucks, vans, or buses), an airplane, a train, or other appropriate vehicle with a passenger cabin. The self-sanitizing systems can be implemented in a vehicle cabin to sanitize surfaces of components in the vehicle cabin that are contacted by occupants of the cabin. The components can include seats, arm rests, door handles, panels, steering wheels to name a few examples. For the sake of simplicity, the following disclosure refers to sanitizing seats.

FIG. 1A to 1E depict an example self-sanitizing system 100. The system 100 includes a sanitizing controller 110, one or more cameras 120, one or more light sources 130, one or more actuation zones 140 (FIG. 1E), and one or more actuators 150. The sanitizing controller 110 can initiate, control, and terminate sanitizing cycles. The sanitizing controller 110 can perform these functions based on signals received from the cameras 120. For example, as described in more detail below, the sanitizing controller 110 can initiate, control, and terminate a sanitizing cycle for the vehicle cabin based on colors detected in images captured by the camera 120.

The sanitizing controller 110 can be a stand-alone microcontroller installed in a vehicle, part of the vehicle's computer system, or part of a camera 120. For example, the camera 120 can be a neuromorphic event-based camera trained to identify change of state events and/or to detect when surfaces of the seats of the vehicle cabin are dirty. In particular, the camera 120 can be trained to detect that an occupant of the vehicle cabin has departed the vehicle cabin or a seat in the cabin. The camera 120 can also be trained to detect contaminants on the seat surfaces.

A stand-alone controller or controller of the vehicle's computer system can be trained to make the same or similar detections based on images received from the camera 120. As described in more detail below, the sanitizing controller 110 can initiate and control a sanitizing cycle in response to detecting one of these change of state events.

The seat surfaces can have integrated thermochromic material, e.g., thread, that changes color with exposure to heat. The seat surfaces can also have integrated photochromic material, e.g., pigment, stain, or dye, that changes color with exposure to UV light. The cameras 120 can be arranged in the vehicle cabin to detect the color of these surfaces. For example, the cameras 120 can be directed at the surfaces of the seat to detect the color of the surfaces. The sanitizing controller 110 can detect the change of state events based on the color of the surfaces. For example, the sanitizing controller 110 can detect that a person has recently departed a seat based on the color of one or more areas of the seat. In particular, the sanitizing controller 110 can detect that a person has recently departed a seat when the color of the thermochromic material is within a specified color range that corresponds to a particular temperature range, e.g., from about 98° F. to about 103° F., or above about 100.4° F. In some implementations, the sanitizing controller 110 can also determine when a person that occupied the seat has a fever, e.g., based on the color of the thermochromic material indicating a temperate in the range above 100° F.

In some implementations, other techniques can be used to detect that a person has occupied a seat, how long the person has occupied the seat, and/or that the person has departed the seat. For example, the camera 120 can use infrared technology to detect body heat and, correspondingly, a seat that was previously occupied. In another example, the sanitizing controller 110 can evaluate images captured by the cameras 120 to detect this information, e.g., using object detection or recognition techniques. The sanitizing controller 110 can determine, using object detection and/or recognition techniques, whether a person has occupied a seat since the last sanitizing cycle and, if so, how long the person occupied the seat. The sanitizing controller 110 can determine, based on whether a person occupied the seat and this duration, whether to initiate another sanitizing cycle and, if so, a duration of the sanitizing cycle.

The use of object detection and/or recognition can be used in combination with the color of the thermochromic material to determine when to initiate a sanitizing cycle, areas of the vehicle cabin to be sanitized, and the duration of the sanitizing cycle for each area. For example, the sanitizing controller 110 can be configured to initiate a sanitizing cycle for an area when at least one, or only when both, techniques indicate that the area should be sanitized.

The sanitizing controller 110 can also detect, in images captured by the cameras 120, contaminants on the seat surfaces. For example, the sanitizing controller 110 can be configured or trained to detect dirt, liquid, objects, or other contamination based on the color of the photochromic material. For example, colors that correspond to temperatures below the ambient temperature of the vehicle cabin may indicate that a cold liquid, e.g., a cold beverage, has been spilt on the surface. In another example, the sanitizing controller 110 may use image processing techniques to detect a stain against the known pattern of a fabric surface.

If a contaminant that cannot be cleaned by UV light is detected, the sanitizing controller 110 can generate a notification that indicates that the cabin is dirty, that a particular surface is dirty, and/or one or more recommended mediation actions based on the contaminant detected. The notification can be sent to a display of the vehicle, a sound system of the vehicle, or a device of a person. The notification can also indicate the detected contaminate.

The sanitizing controller 110 can also detect when a surface has been sufficiently sanitized based on the color of the photochromic material. For example, the sanitizing controller 110 can detect that a surface has been sufficiently sanitized when the color of the photochromic material is within a specified color range corresponding to exposure to a particular amount of UV light or exposure to UV light for a particular duration of time. The sanitizing controller 110 can terminate a sanitizing cycle when the color of the photochromic material is within the particular color range. For example, the sanitizing controller 110 can terminate the sanitizing cycle when the entire surface or at least a threshold percentage of the surface is within the specified color range.

During a sanitizing cycle, the sanitizing controller 110 can activate the light sources 130. The light sources 130 can include one or more UV (100 to 400 nm) or far-UVC (200 to 230 nm, e.g., 222 nm) lights. The light sources 130 can be arranged within the cabin to illuminate the seat surfaces to be sanitized. For example, the light sources of a car's cabin can be installed on the dash to sanitize the surfaces of the front seats and installed on the seat backs of the front seats to sanitize the surfaces of the next row of seats. The light sources 130 can also be installed in other areas, such as the ceiling, floor, on doors, on consoles, etc.

To better sanitize the surfaces of the vehicle cabin, the self-sanitizing system 100 can include actuation zones 140 and actuators 150 that adjust the shape, orientation, and position of the components of the vehicle cabin. A seat can include one or more actuation zones 140 embedded under or behind the surface of the seat. Each actuation zone 140 can include actuation cells that each raise a portion of the flexible seat surface to temporarily alter its shape. The sanitizing controller 110 can control the actuation zones 140 to continuously change the shape of the surface during a sanitizing cycle. For example, the sanitizing controller 110 can activate and deactivate the cells of an actuation zone in sequence to change the shape of the surface.

Each actuation cell can be embedded under the surface and can include an electromechanical device that, when actuated by a control signal, pushes a portion of the surface outwards. For example, the electromechanical device can be a small or micro linear actuator embedded under the surface.

The sanitizing controller 110 can also activate actuators 150 of the seats to change the position or orientation of the seats. For example, seats in many cars include actuators that enable occupants to adjust the seatback (e.g., tilt the seatback or adjust the lumbar support), move the seat forward and backwards, and/or raise and lower the entire seat. The sanitizing controller 110 can be in data communication with the actuators, e.g., via the vehicle's computing system or directly vie wires or a wireless connection, to change the various seat adjustments.

The sanitizing controller 110 can make these adjustments as a regular part of the sanitizing cycle, e.g., to sanitize areas that would not be illuminated by the light sources in their normal positions. The sanitizing controller 110 can also make these adjustments in response to detecting that an area of a surface has not been sufficiently sanitized, e.g., based on the color of the photochromic material at those areas. For example, if the front surface of a seat cushion has a color indicating that it has not been sufficiently sanitized, the sanitizing controller 110 can cause the seat to tilt back, thereby raising this surface towards the light source.

Figure 1B:
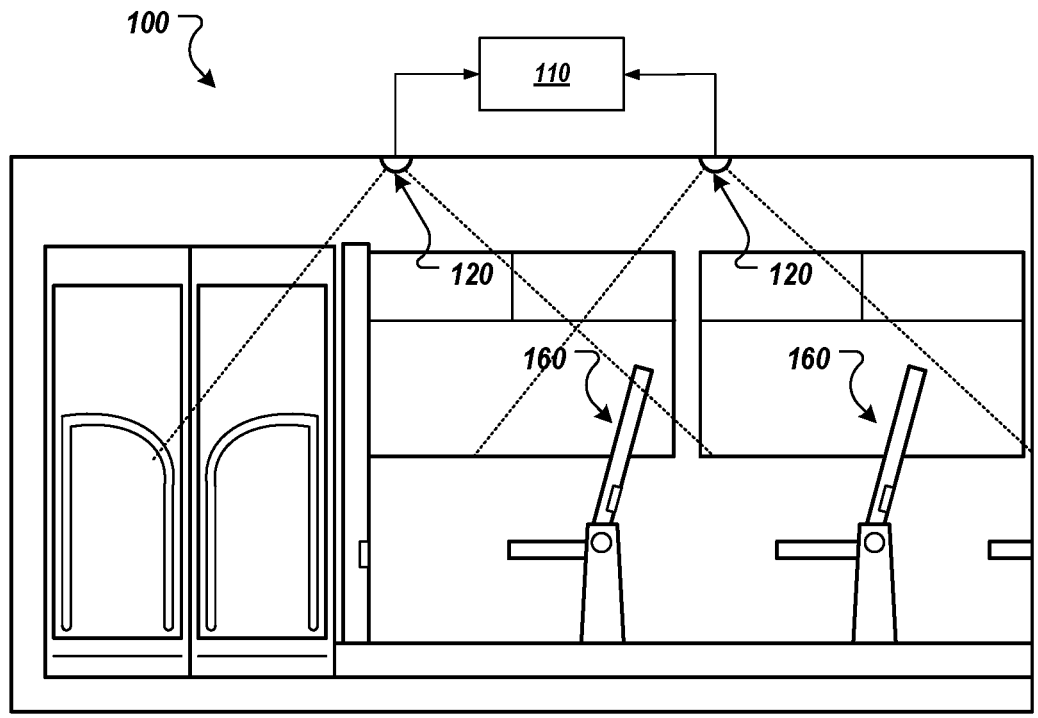
Figure 1C:
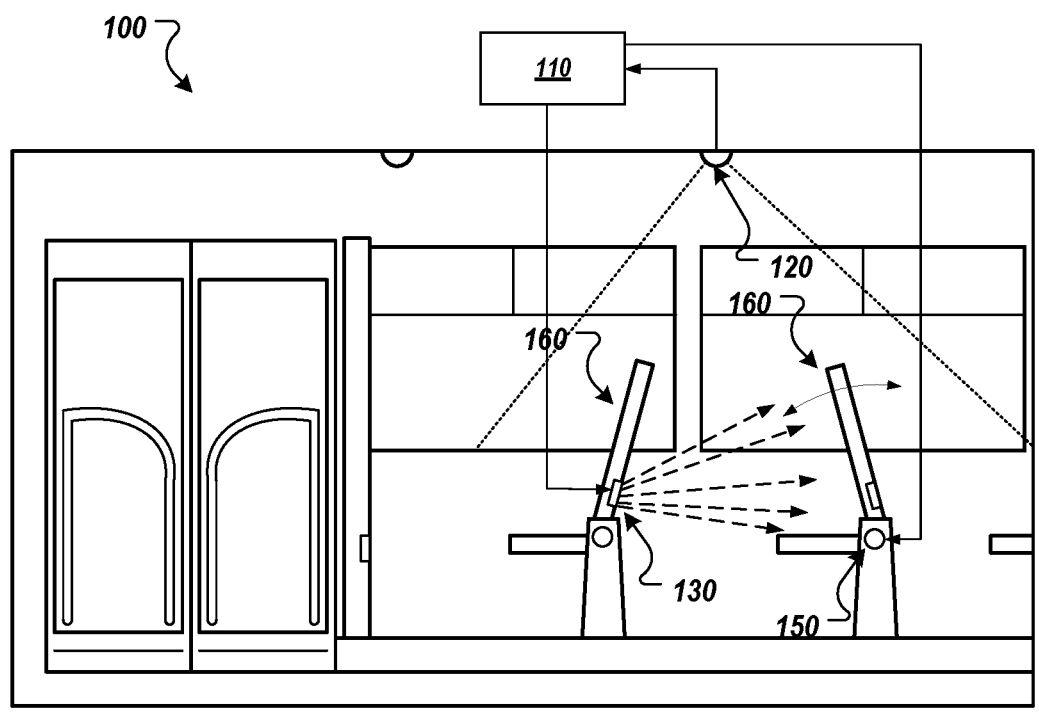
Figure 1D:
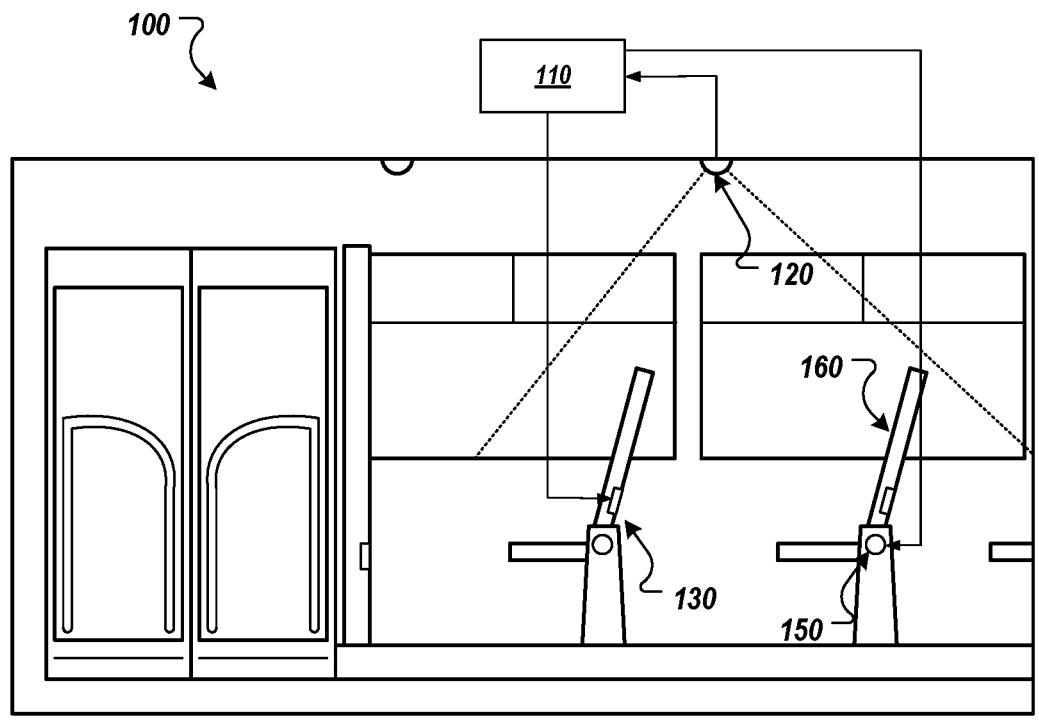
Figure 1E:
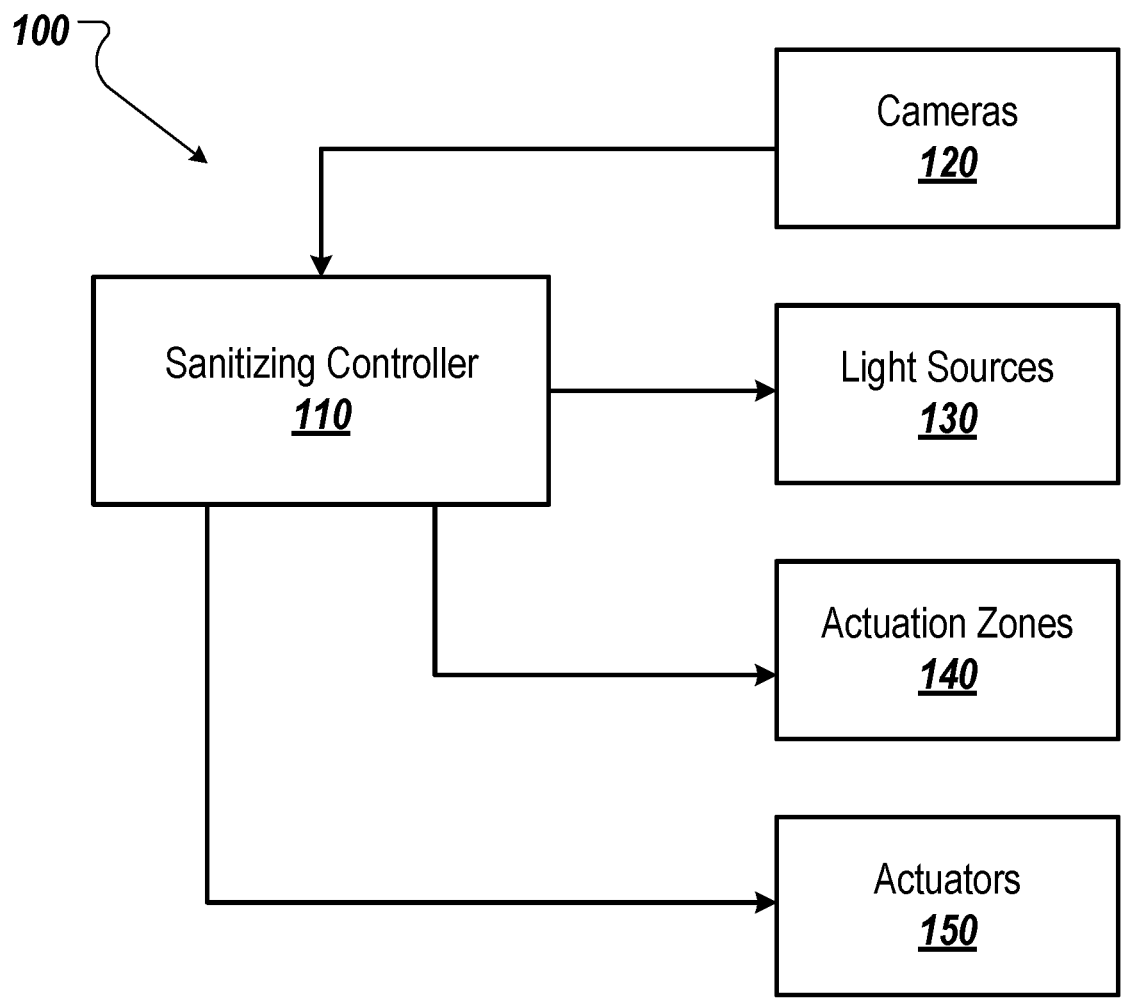

FIGS. 1A to 1D depict an example implementation of the self-sanitizing system 100 in a bus, whereas FIG. 1E depicts a block diagram of the system 100. The system 100 includes a sanitizing controller 110, one or more cameras 120, one or more light sources 130, one or more actuation zones (not shown), and one or more actuators 150. The bus includes, e.g., a row of adjustable passenger seats 160. The seat 160 includes a seatback 160a, a seat portion 160b, and a base 160c. The actuator 150 is configured to move the seatback 160a relative to the seat portion 160b and the base 160c (FIG. 1C).

FIG. 1A depicts the system 100 in an initial state in which a passenger P is sitting in the second seat 160. The cameras 120 are mounted on the ceiling of the bus and are oriented to capture images of the seats 160. The sanitizing controller 110 is configured to receive images captured by the cameras 120 and determine that the passenger P is present based on, e.g., infrared technology, event tracking technology, object detection in images, or any of the other techniques described above. As previously described, the sanitizing controller 110 can initiate, control, and terminate sanitizing cycles based on signals received from the cameras 120. In some implementations, the sanitizing controller 110 is configured to prevent initiation of the sanitizing cycle or to terminate a sanitizing cycle that has started if a person is detected in a sanitizing zone. For example, the sanitizing zone can correspond to an area exposed to the UV light emitted by a particular sanitizing light source.

FIG. 1B depicts the system 100 after the passenger P has departed the seat 160 and the associated sanitizing zone. In some instances, the sanitizing controller 110 is configured to determine whether an unoccupied sanitizing zone has been used since the previous sanitizing cycle. For example, the seat 160 closest to the door of the bus is shown to be unoccupied in both FIGS. 1A and 1B. The sanitizing controller 110 may monitor images from the corresponding ceiling-mounted camera 120 over a period of time (e.g., in the form of a continuous video feed or a series of images) to determine that the seat in question has not been occupied and does not require sanitizing. Although FIG. 1A to 1D depict ceiling-mounted cameras 120, in other implementations, the cameras 120 may be mounted differently, e.g., as described in reference in FIG. 2.

As previously described, the sanitizing controller 110 can be configured to prevent a sanitizing cycle from starting or terminate an active sanitizing cycle if a person is detected in a sanitizing zone. This can potentially prevent unwanted exposure to the light emitted from the sanitizing light sources 130. In some cases, unwanted exposure may be further reduced using additional contextual information to prevent sanitizing cycles. For example, if the bus is travelling along a busy bus route during the middle of the day, a new passenger may enter an unoccupied sanitizing zone at any time. In such a case, the sanitizing controller 110 may not initiate a sanitizing cycle until additional safety criteria are met. Conversely, the bus may have departed the final stop for the night and is on its way back to a terminal. Similarly, a system 100 implemented in a ride sharing vehicle may detect that the rear cabin of the vehicle is now unoccupied and simultaneously receive the information from a payment system that the ride has ended. In such cases, a person is relatively unlikely to suddenly re-enter the sanitizing zone, and the sanitizing controller 110 may initiate a sanitizing cycle as soon as the controller detects that the sanitizing zone is unoccupied.

In some instances, the sanitizing controller 110 in FIG. 1B is configured to determine whether a sanitizing cycle is necessary based on any of the previously described techniques. For example, the controller 110 can be configured to determine how long the passenger P was sitting on the seat 160 and initiate the sanitizing cycle if the seated duration is above a previously determined threshold value. In other cases, thermochromic material may be integrated in the surface of the seat 160, as described below in more detail. The sanitizing controller 110 can detect that a person has recently departed a seat when the color of the thermochromic material is within a specified color range that corresponds to a particular temperature range, e.g., from about 98° F. to about 103° F., or above about 100.4° F.

The sanitizing cycle can also be triggered when the controller 110 detects that the surface of the seat 160 is dirty. The seat surfaces can also have integrated photochromic material, e.g., pigment, stain, or dye, that changes color with exposure to UV light. The sanitizing controller 110 can be trained to detect dirt, liquid, objects, or other contamination based on the color of the photochromic material.

FIG. 1C depicts the system 100 once the sanitizing cycle has been initiated. Specifically, a sanitizing light source 130 is arranged in front of each seat 160. During a sanitizing cycle, the sanitizing controller 110 can activate the light sources 130. The light sources 130 can include one or more UV (100 to 400 nm) or far-UVC (200 to 230 nm, e.g., 222 nm) lights. Although FIGS. 1A to 1D depict a single sanitizing light source 130 for each seat 160, other implementations can include a greater number of sanitizing light sources 130 and/or sanitizing light sources 130 that are installed in other areas, such as the ceiling, floor, on doors, etc.

During the sanitizing cycle, the sanitizing controller 110 sends instructions to the actuator 150 integrated in the seat 160 to move the seatback 160a, as shown by the double-headed arrow. The movement of the seatback 160a may allow different sections of the seatback 160a to be exposed to the sanitizing light emitted by the sanitizing light source 130. In addition to the movement depicted in FIG. 1C, the sanitizing controller 110 can send instructions to the actuator 150 to perform a pre-defined sequence of adjustments or to perform specific adjustments in response to the sanitizing controller 110 detecting that certain portions of the seat 160 have not been sufficiently sanitized.

Figure 4:
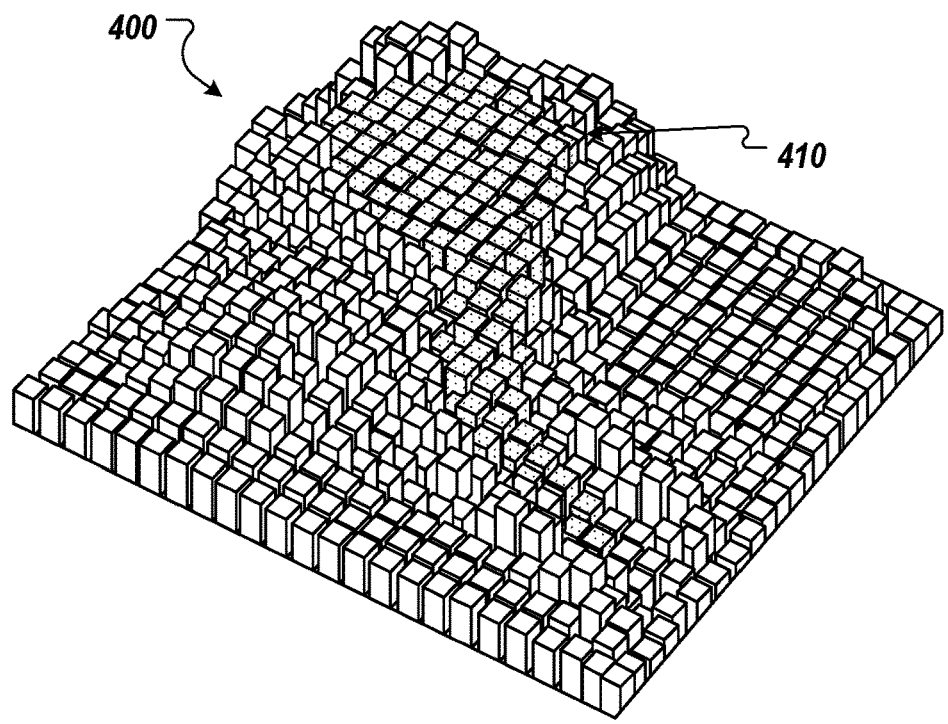
FIG. 4 depicts example cells of an actuation zone.

Although not specifically shown in FIGS. 1A to 1D, the seats 160 may include actuation zones 140 similar to the cells shown in FIG. 4. During the sanitizing cycle, the sanitizing controller 110 can activate one or more of the actuation zones 140 to change the shape of the seat surface, as described in reference to FIG. 4.

Throughout the sanitizing cycle, the sanitizing controller 110 can be configured to monitor the progress of the sanitizing cycle via images from the cameras 120. As the sanitizing controller 110 progresses through a pre-defined sequence of actuation zones 140 and/or adjustments via the actuator 150, the sanitizing controller 110 may determine that the relevant sections of the seat 160 have been sufficiently sanitized during previous adjustments or activations. In such a case, the sanitizing controller 110 can be configured to "skip" certain portions of the sequence to shorten the overall duration of the sanitizing cycle, which conserves power, and reduces wear on actuators.

In FIG. 1D, the sanitizing controller 110 has terminated the sanitizing cycle. As previously described, the sanitizing cycle may be terminated when a specific duration has elapsed or a pre-defined sequence has been completed. In other implementations, the sanitizing controller 110 may be configured to determine that the target seat 160 has been sufficiently sanitized based on images captured by the cameras 120, e.g., based on the color of the surfaces as described above.

Figure 2:
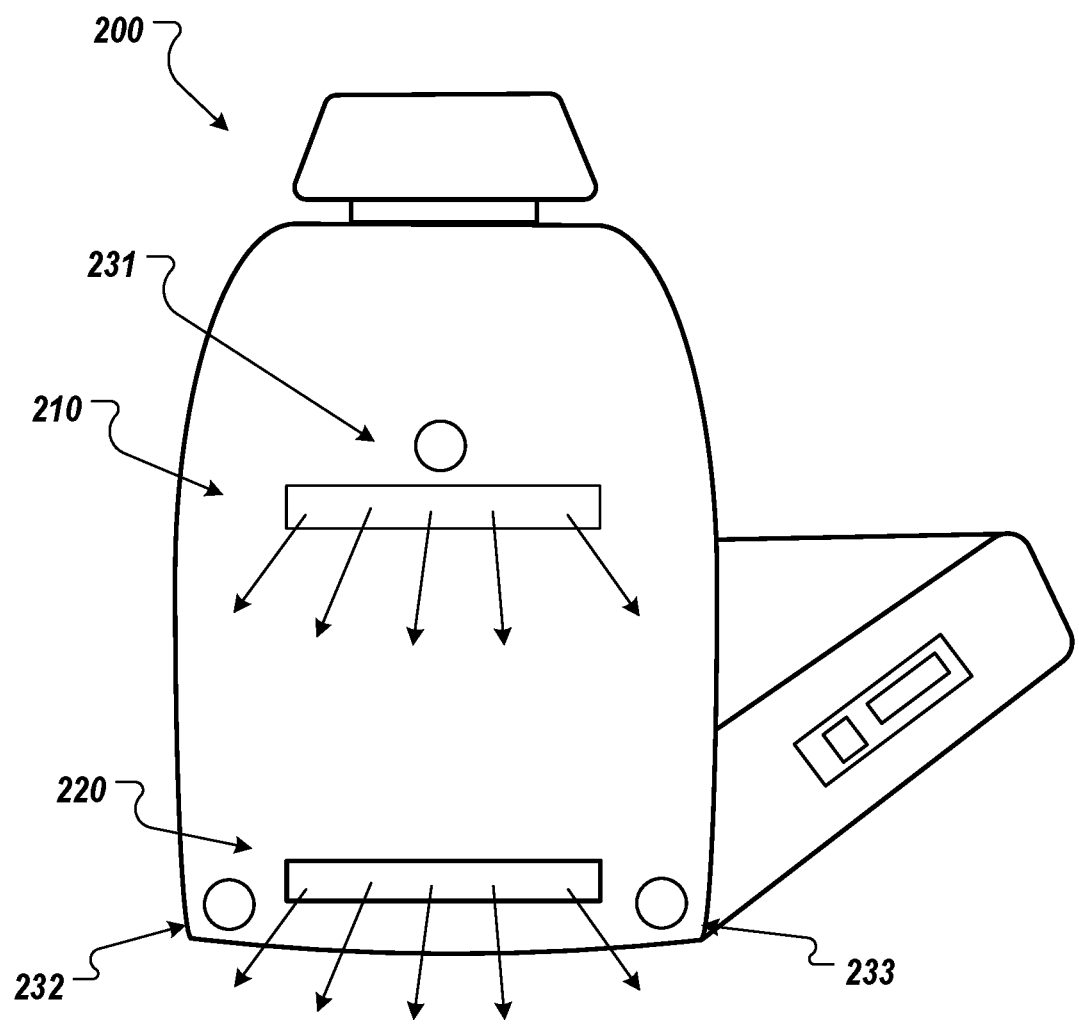
FIG. 2 depicts an example seatback with sanitizing light sources.

FIG. 2 depicts an example seatback 200 with sanitizing light sources 210 and 220. The seatback 200 can be a seatback of seats in an automobile, airplane, train, or other vehicle. The light sources 210 and 220 can include UV or far-UVC lights that sanitize the surfaces of a seat located behind the seatback 200. In this example, the seatback 200 includes a first light source 210 that is located above a second light source 220. The first light source 210 can sanitize the seatback of the other seat and the second light source 220 can sanitize the lower portion of the other seat.

The seatback 200 also includes cameras 231-233. The cameras can be used to detect colors of the other seat for the purposes of initiating, controlling, and terminating sanitizing cycles. Each camera 231-233 can be used to detect the color of a particular area of the other seat.

Figure 3:
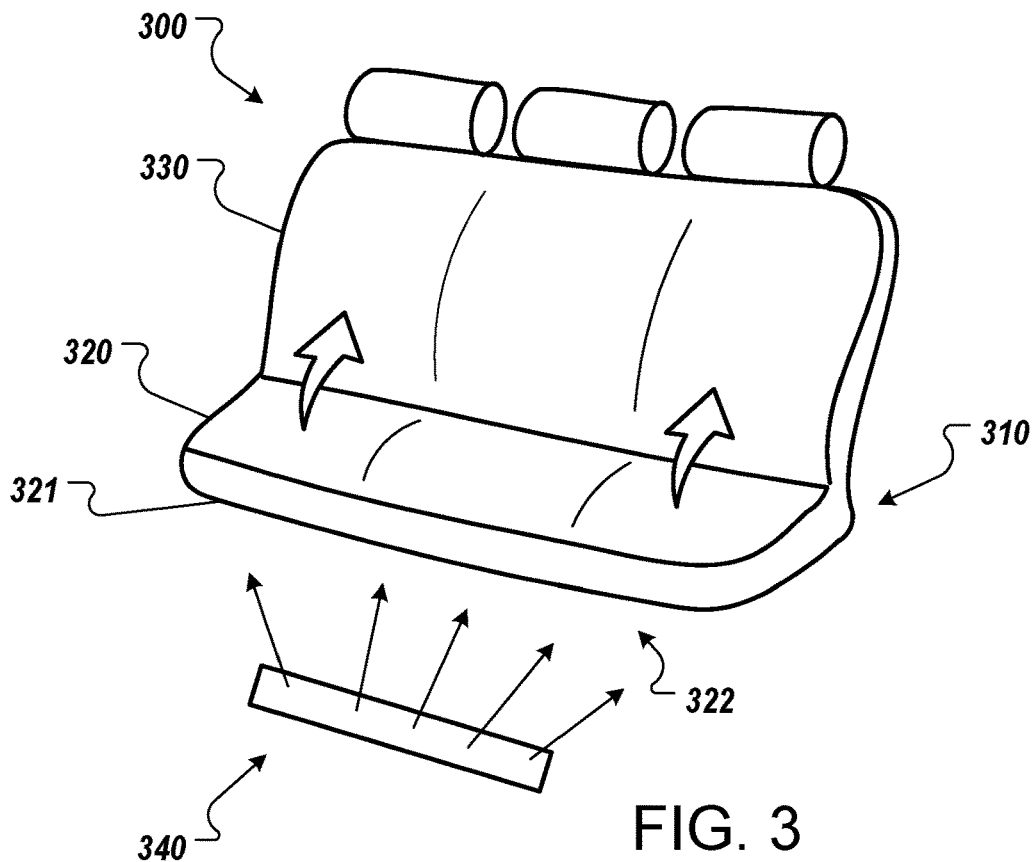
FIG. 3 depicts an example adjustable seat.

FIG. 3 depicts an example adjustable seat 300. The adjustable seat 300 includes a seat portion 320 and a seatback 330. The adjustable seat 300 also includes an actuator 310 that lifts and lowers the seat 300, e.g., the entire seat 300 including the seat portion 320 and the seatback 330. The sanitizing controller 110 can control the actuator 310 to lift the seat 300 during a sanitizing cycle so that a light source 340 can sanitize a front portion 321 of the seat portion 320 or the underside 322 of the seat portion 330. The sanitizing controller 110 can lift the seat 300 after sanitizing the seatback 330, e.g., as part of a regular sanitizing procedure, or in response to detecting that the front portion 321 or underside 322 has not been sufficiently sanitized.

The seat 300 can also include actuation zones in the seatback 330 and/or in the seat portion 320. The actuation zones change the shape, orientation, and/or position of the surfaces of the seatback 330 and/or the seat portion 320. The actuation zones can be located throughout the seatback 330 and/or seat portion 320, or in particular areas that are typically more difficult to sufficiently sanitize. Each actuation zone can be controlled separately to provide different levels or amounts of sanitization to different areas of the seatback 330 and/or seat portion 320.

FIG. 4 depicts example cells 410 of an actuation zone 400. The actuation zone 400 can be used in the seat 300 of FIG. 3 or in surfaces of other components of a vehicle cabin. As shown in FIG. 4, the cells 410 can be raised and lowered to raise or lower the surface of a seat. For example, if the actuation zone 400 is embedded under the seat portion 320, the cells 410 can raise and lower areas of the seat portion 320.

The sanitizing controller 110 can raise and lower the various cells 410 in a sequence to continuously or periodically change the shape of a surface. For example, the sanitizing controller 110 can raise and lower the cells 410 such that is appears that a raised area is moving under the surface of the seat portion 320 or behind the seatback 330. The raised area can be moved side to side, diagonally, and/or in other patterns to raise each part of the surface to ensure sufficient sanitization of the entire surface.

Figure 5B:
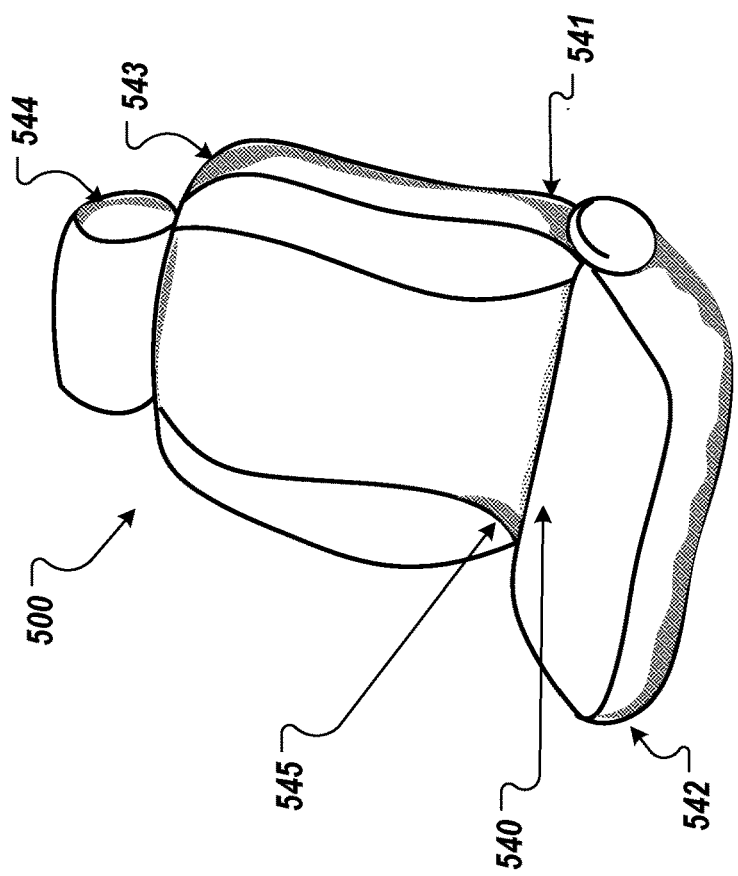
FIGS. 5A and 5B depict a seat with thermochromic material and photochromic material integrated in the surfaces of the seat.
Figure 5A:
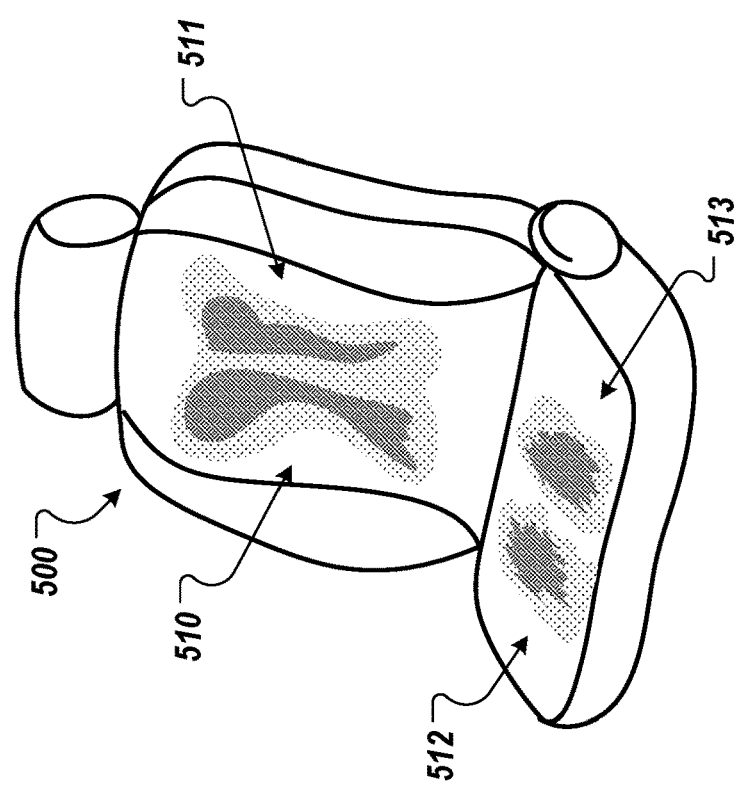

FIGS. 5A and 5B depict a seat 500 with thermochromic material and photochromic material integrated in the surfaces of the seat. Referring to FIG. 5A, the thermochromic material has changed color in a few areas 510-513 in response to exposure to heat. In particular, the thermochromic material has changed color in areas 510-513 that would be covered by a person sitting in the seat 500. The sanitizing controller 110 can detect this color change based on images captured by a camera 120 and initiate a sanitizing cycle to sanitize the surfaces of the seat. For example, the sanitizing controller 110 can detect that the color of these areas are within a specified color range corresponding to a temperature range indicative of a person having recently occupied the seat 500, while the color of the other areas are not within the specified color range.

Referring to FIG. 5B, the photochromic material has changed color in a few areas, including areas 540-545, in response to exposure to UV light. The sanitizing controller can similarly detect this color change and terminate the sanitizing cycle in response to detecting the change. For example, the sanitizing controller can detect that the color is a particular color or within a specified color range corresponding to a specific amount of UV or far-YVC exposure. This color change can also signal to the next occupant of the vehicle cabin that the seat 500 has been sanitized.

Figure 6:
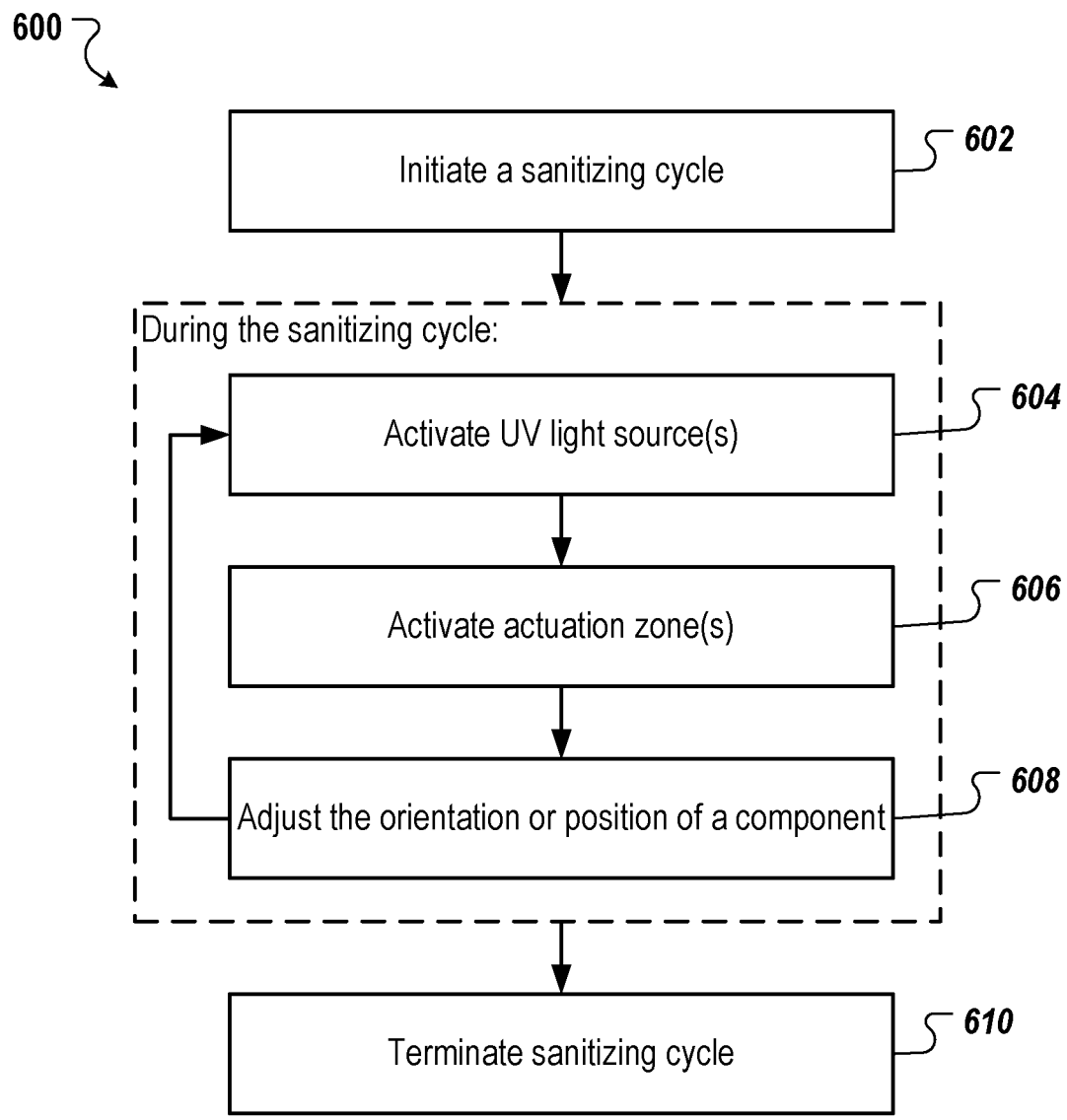
FIG. 6 is a flow chart of an example process for performing a self-sanitizing cycle.

FIG. 6 is a flow chart of an example process 600 for performing a self-sanitizing cycle. The process can be performed by the sanitizing controller 110 of FIGS. 1A to 1E.

The sanitizing controller initiates a sanitizing cycle for sanitizing one or more surfaces of one or more components of a vehicle cabin (602). For example, the sanitizing controller can initiate the sanitizing cycle to sanitize the surfaces of seats, arm rests, door handles, panels, or other appropriate components of the vehicle cabin.

In some implementations, the sanitizing controller can initiate the sanitizing cycle in response to detecting a change of state event. The sanitizing controller can detect, as the change of state event, that an occupant of the vehicle cabin has departed the vehicle cabin or a particular seat in the vehicle cabin. In another example, the sanitizing controller can detect, as the change of state event, that the cleanliness state of the vehicle has changed from a clean vehicle cabin to a dirty vehicle cabin. The sanitizing controller can detect these change of state events based on the color of thermochromic material integrated in the surface of the components. For example, the sanitizing controller can determine that an occupant has departed a seat or that a surface of a seat is dirty based on the color of the thermochromic material being within a respective specified color range. In another example, the sanitizing controller can detect these change of state events based on detecting dirt, liquid, or other contaminants in images captured by a camera.

During the sanitizing cycle, the sanitizing controller activates one or more UV light sources (604). The UV light sources can include UV or far-UVC light sources. The light sources can be arranged in the vehicle cabin to direct UV light onto the surfaces of the components to be sanitized during the sanitizing cycle.

During the sanitizing cycle, the sanitizing controller activates one or more actuation zones (606). The sanitizing controller can activate the actuation zones to change the shape, orientation, and/or position of the surfaces being sanitized, e.g., so that the UV light sufficiently sanitizes each area of the surfaces and/or to direct contaminants from the surface. For example, the surfaces can include channels for directing the contaminants from the surfaces. In the process 600 of FIG. 6, the one or more UV light sources are activated prior to the one or more actuation zones. In some implementations, the one or more UV light sources are activated after the one or more actuation zones.

The sanitizing controller can raise and lower the cells of the actuation zones in sequences to change the shape of the surfaces. For example, the sanitizing controller can continuously raise and lower the cells during the sanitizing cycle or during a particular portion of the sanitizing cycle.

During the sanitizing cycle, the sanitizing controller adjusts the position and/or orientation of one or more components of the vehicle cabin (608). The sanitizing controller can control actuators of the components to make these adjustments. For example, the sanitizing controller can cause a seat to more bank and forth, to recline and incline, to raise or lower, and/or make other appropriate adjustments depending on the controls available for the particular seat being sanitized.

The sanitizing controller can perform a sequence of adjustments during the sanitizing cycle. For example, the sanitizing controller can lower a seat during a first portion of the sanitizing cycle to sanitize an upper portion of the seat using stationary light sources. The sanitizing controller can then raise the seat during a second portion of the sanitizing cycle to sanitize a lower portion of the seat during a second portion of the sanitizing cycle.

The sanitizing controller can also adjust the portion and/or orientation of a component based on detecting that an area of the surface of the component has not been sufficiently sanitized. For example, the sanitizing controller can receive images from one or more cameras and evaluate the color of the photochromic material integrated in the surface. If the color is not within a specified color range that indicates sufficient sanitization, the sanitizing controller can adjust the position and/or orientation of the component such that the area is closer to or in more direct line of sight of one of the light sources. The sanitizing controller can also activate the actuation zones in this area to better sanitize each portion of the area.

In some implementations, the sanitizing controller can sanitize multiple surfaces, components, or areas of the vehicle cabin in sequence. For example, once one area is sanitized, the sanitizing controller can proceed to another area. In this example, the sanitizing controller can return to operation 604 (or 606 if using the same light source) to sanitize another area by activating actuation zones under or behind the surface(s) of that area and/or adjusting the orientation and/or position of the component(s) in that area.

The sanitizing controller terminates the sanitizing cycle (610). For example, the sanitizing controller can evaluate the color of the photochromic material integrated in the surfaces being sanitized. If the color of each area of the surface, or at least a threshold percentage of the areas, is within a specified color range that indicates sufficient sanitization, the sanitizing controller can terminate the sanitizing cycle. If multiple areas are cleaned in sequence, the sanitizing controller can terminate the sanitizing cycle after all areas to be sanitized have been sufficiently sanitized.

Figure 7A:
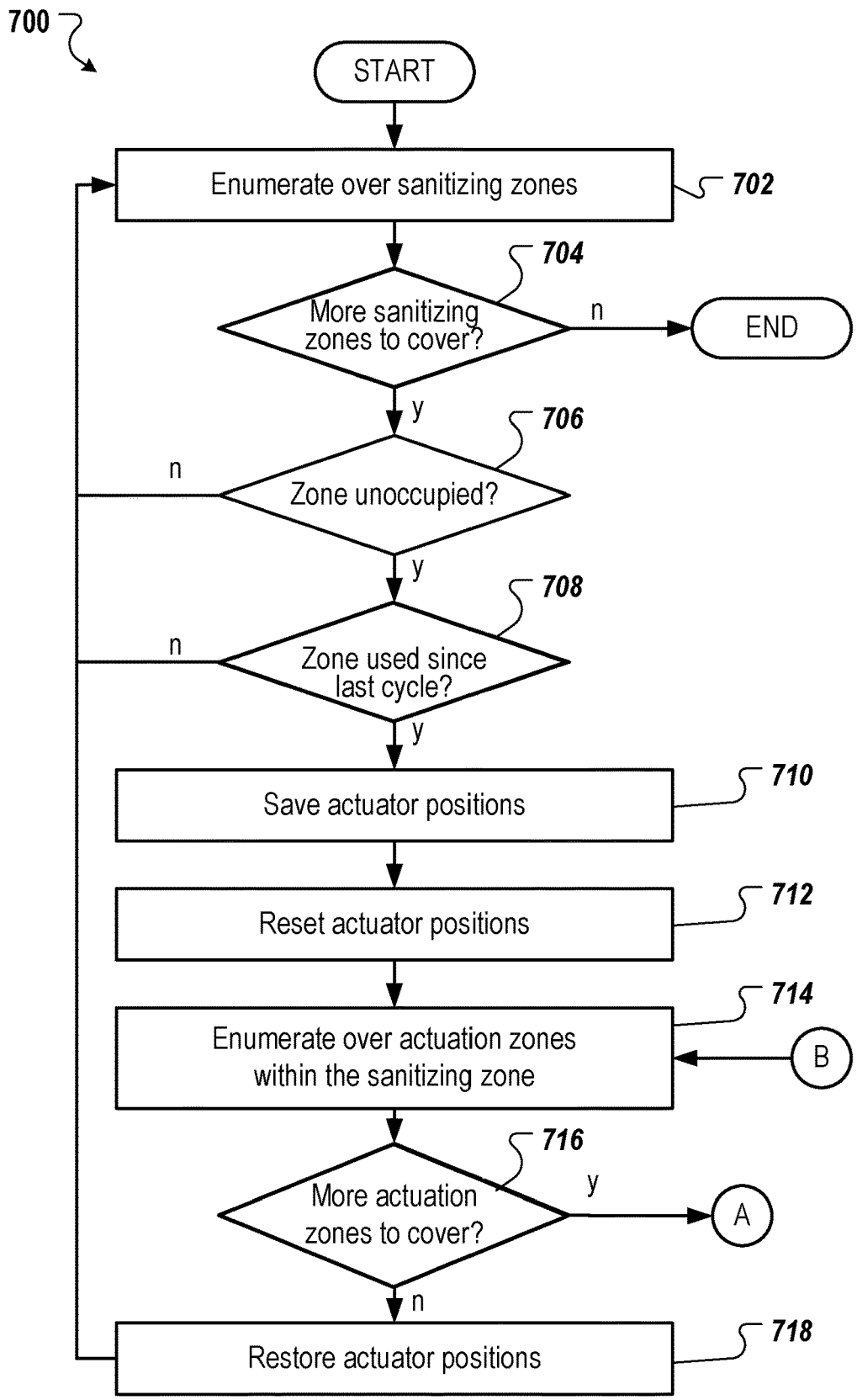
FIGS. 7A and 7B are a flow chart of a further example process for performing a self-sanitizing cycle.
Figure 7B:
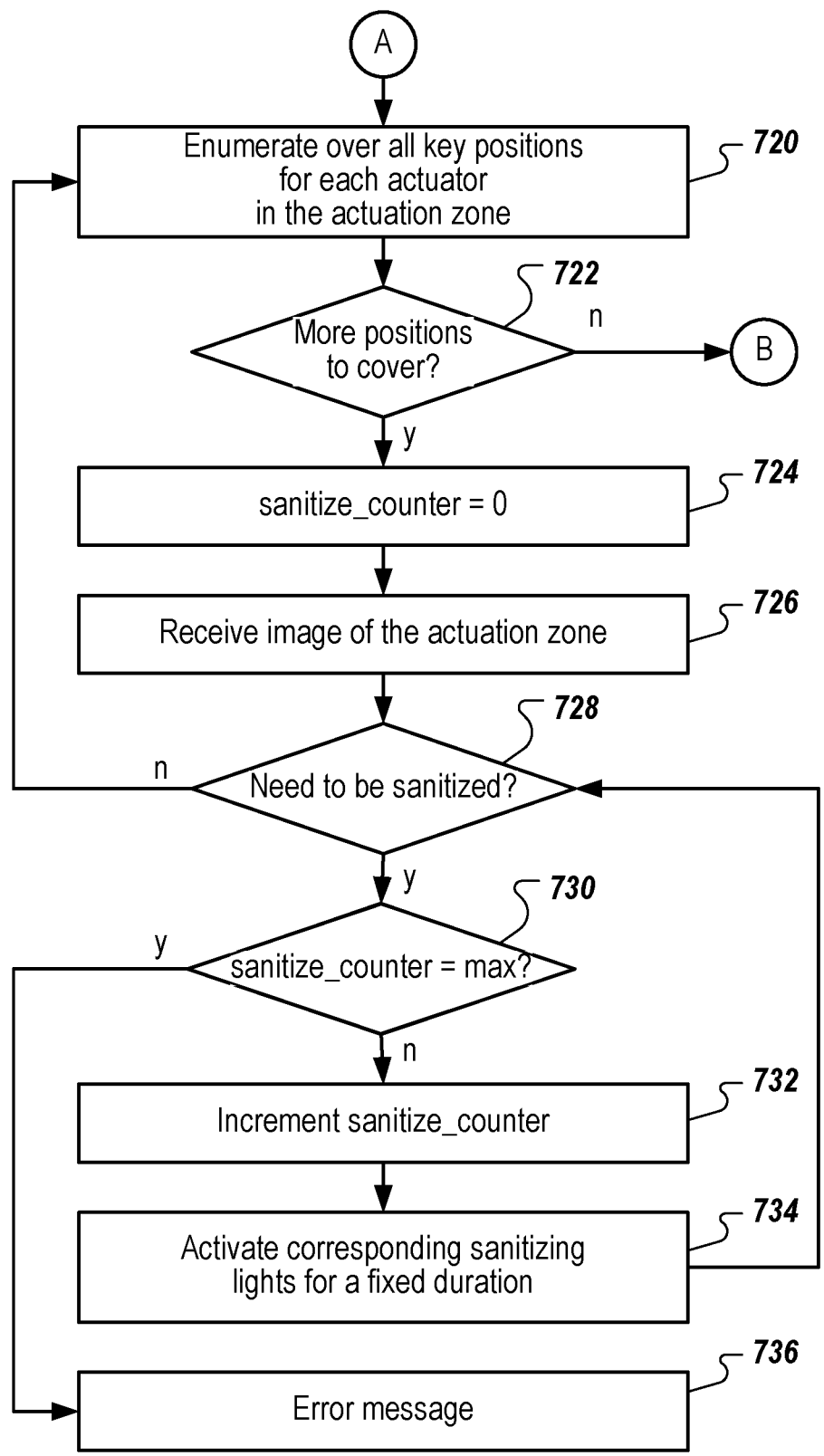

FIGS. 7A and 7B show a flow chart of a further example process 700 for performing a self-sanitizing cycle. The process 700 can be performed by the sanitizing controller 110 of FIGS. 1A to 1E.

The sanitizing controller can enumerate over a plurality of sanitizing zones (702). For example, the sanitizing zones may be associated with individual seats 160 in the system 100 depicted in FIGS. 1A to 1D. Once the sanitizing controller has evaluated all of the sanitizing zones, the process 700 is complete (704).

For each sanitizing zone, the sanitizing controller may evaluate whether the zone is unoccupied based on any of the techniques described above (706). If the sanitizing zone is determined to be unoccupied, the sanitizing controller evaluates whether the sanitizing zone has been used since the previous sanitizing cycle (708). If the sanitizing zone has not been used, the controller 110 may deem the sanitizing zone to be sufficiently sanitized and move onto the next sanitizing zone in the sequence.

For each sanitizing zone, the sanitizing controller may initially save the position of all actuators within each of the actuation zones within the sanitizing zone (710). In this context, "actuator" can refer to individual cells or movers within an actuation zone 140, for example. The sanitizing controller can optionally reset each of the actuator positions (712). The sanitizing controller can then enumerate over each of the actuation zones within the sanitizing zone (714) and restore the actuator positions to the saved actuator positions once all actuation zones have been covered (708, 718).

Referring now to FIG. 7B, the sanitizing controller can enumerate over a number of predetermined positions that is associated with each actuator in the actuation zone (720). For each position, the sanitizing controller can use a sanitizing counter to control the number of attempts to sanitize the actuation zone (724, 730, 732). The sanitizing controller can receive an image (e.g., from cameras 120) that includes at least the current actuation zone (726). The sanitizing controller can determine whether the image shows that the actuation zone needs to be sanitized (728). If the sanitizing counter is below the maximum value (730), the controller increments the counter and activates the sanitizing lights for a fixed duration (732, 734). If the sanitizing counter is above the maximum value, the sanitizing controller determines that the system has tried too many times to clean the relevant section and failed. In this case, the sanitizing controller may output an error message (736).

Although the process 700 depicts a sequence that cycles through all sanitizing zones, all actuation zones within each sanitizing zone, and all actuator positions within each actuation zone, some implementations of the process 700 may execute these loops in parallel to one another to reduce the overall duration of the sanitizing cycle.

Embodiments of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory program carrier for execution by, or to control the operation of, data processing apparatus. Alternatively or in addition, the program instructions can be encoded on an artificially generated propagated signal, e.g., a machine generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them. The computer storage medium is not, however, a propagated signal.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) monitor, an LCD (liquid crystal display) monitor, or an OLED display, for displaying information to the user, as well as input devices for providing input to the computer, e.g., a keyboard, a mouse, or a presence sensitive display or other surface. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending resources to and receiving resources from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client server relationship to each other.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method, comprising:
   initiating a sanitizing cycle for sanitizing one or more surfaces of one or more components of a vehicle cabin;
   during the sanitizing cycle:
   activating one or more ultraviolet (UV) light sources configured to illuminate at least a portion of each of the one or more surfaces; and
   adjusting at least one of a shape, a position, or an orientation of at least one surface of the one or more surfaces with respect to the one or more UV light sources, wherein by adjusting the shape of the at least one surface with respect to the one or more UV light sources one or more actuation zones of the at least one surface are activated, and wherein each actuation zone of the one or more actuation zones comprises a plurality of cells that adjust the shape of the at least one surface multiple times during the sanitizing cycle; and
   terminating the sanitizing cycle based on the adjustment.

2. The method of claim 1, wherein the one or more UV light sources comprise one or more far-UVC light sources.

3. The method of claim 1, wherein initiating the sanitizing cycle comprises:
 detecting a change of state event indicating (i) that an occupant of the vehicle cabin has departed the vehicle cabin and (ii) a change of state from a clean vehicle cabin to a dirty vehicle interior; and
 initiating the sanitizing cycle in response to detecting the change of state event.

4. The method of claim 3, wherein detecting the change of state event comprises detecting that a color of thermochromic material of the at least one surface is within a specified color range.

5. The method of claim 1, wherein initiating the sanitizing cycle comprises detecting that a sanitizing zone that comprises the one or more surfaces is unoccupied.

6. The method of claim 1, wherein terminating the sanitizing cycle comprises:
 detecting that a color of photochromic material of the at least one surface is within a specified color range; and
 terminating the sanitizing cycle in response to detecting that the color of the photochromic material of the at least one surface is within the specified color range.

7. The method of claim 1, wherein adjusting at least one of the shape, the position, or the orientation of the at least one surface with respect to the one or more UV light sources comprises:
 determining that an area of the at least one surface of a component of the one or more components has not been sufficiently sanitized; and
 adjusting the orientation or the position of the component such that the area is illuminated by the one or more UV light sources.

8. The method of claim 1, further comprising:
 detecting a contaminant on the at least one surface; and
 generating a notification that indicates that the vehicle cabin is in an unclean state, wherein the notification indicates one or more recommended manual interventions to clean the vehicle cabin.

9. A system, comprising:
 one or more processors; and
 one or more memory devices interoperably coupled with the one or more processors and having tangible, non-transitory, machine-readable media storing one or more instructions that, when executed by the one or more processors, cause the one or more processors to perform operations comprising:
  initiating a sanitizing cycle for sanitizing one or more surfaces of one or more components of a vehicle cabin;
  during the sanitizing cycle:
   activating one or more ultraviolet (UV) light sources configured to illuminate at least a portion of each of the one or more surfaces; and
   adjusting at least one of a shape, an orientation, or a position of at least one surface of the one or more surfaces with respect to the one or more UV light sources, wherein by adjusting the shape of the at least one surface with respect to the one or more UV light sources comprises activating one or more actuation zones of the at least one surface are activated, and wherein each actuation zone of the one or more actuation zones comprises a plurality of cells that adjust the shape of the at least one surface multiple times during the sanitizing cycle; and
  terminating the sanitizing cycle based on the adjustment.

10. The system of claim 9, wherein the one or more UV light sources comprise one or more far-UVC light sources.

11. The system of claim 9, wherein initiating the sanitizing cycle comprises:
 detecting a change of state event indicating (i) that an occupant of the vehicle cabin has departed the vehicle cabin and (ii) a change of state from a clean vehicle cabin to a dirty vehicle interior; and
 initiating the sanitizing cycle in response to detecting the change of state event.

12. The system of claim 11, wherein detecting the change of state event comprises detecting that a color of thermochromic material of the at least one surface is within a specified color range.

13. The system of claim 9, wherein initiating the sanitizing cycle comprises detecting that a sanitizing zone that comprises the one or more surfaces is unoccupied.

14. The system of claim 9, wherein terminating the sanitizing cycle comprises:
 detecting that a color of photochromic material of the at least one surface is within a specified color range; and
 terminating the sanitizing cycle in response to detecting that the color of the photochromic material of the at least one surface is within the specified color range.

15. The system of claim 9, wherein adjusting at least one of the shape, the orientation, or the position of the at least one surface with respect to the one or more UV light sources comprises:
 determining that an area of the at least one surface of a component of the one or more components has not been sufficiently sanitized; and
 adjusting the orientation or the position of the component such that the area is illuminated by the one or more UV light sources.

16. The system of claim 9, wherein the operations comprise:
 detecting a contaminant on the at least one surface; and
 generating a notification that indicates that the vehicle cabin is in an unclean state, wherein the notification indicates one or more recommended manual interventions to clean the vehicle cabin.

17. A non-transitory, computer-readable medium storing one or more instructions executable by a computer system to perform operations comprising:
 initiating a sanitizing cycle for sanitizing one or more surfaces of one or more components of a vehicle cabin;
 during the sanitizing cycle:
  activating one or more ultraviolet (UV) light sources configured to illuminate at least a portion of each of the one or more surfaces; and
  adjusting at least one of a shape, an orientation, or a position of at least one surface of the one or more surfaces with respect to the one or more UV light sources, wherein by adjusting the shape of the at least one surface with respect to the one or more UV light sources one or more actuation zones of the at least one surface are activated, and wherein each actuation zone of the one or more actuation zones comprises a plurality of cells that adjust the shape of the at least one surface multiple times during the sanitizing cycle; and
 terminating the sanitizing cycle based on the adjustment.

18. The non-transitory, computer-readable medium of claim 17, wherein initiating the sanitizing cycle comprises:
 detecting a change of state event indicating (i) that an occupant of the vehicle cabin has departed the vehicle cabin and (ii) a change of state from a clean vehicle cabin to a dirty vehicle interior; and initiating the sanitizing cycle in response to detecting the change of state event.

\* \* \* \* \*